United States Patent
Kaufmann

(10) Patent No.: US 6,582,731 B1
(45) Date of Patent: Jun. 24, 2003

(54) HARD CANDY WITH PLAQUE-NEUTRALIZING EFFECT COMPRISING ALKALI METAL MONOPHOSPHATE

(76) Inventor: Konrad Kaufmann, Rebbergshasse 32, Dietikon 2H (CH), 8953

(*) Notice: Subject to any disclaimer, the term of this patent is extended or adjusted under 35 U.S.C. 154(b) by 52 days.

(21) Appl. No.: 09/654,358

(22) Filed: Sep. 1, 2000

Related U.S. Application Data

(63) Continuation-in-part of application No. 09/200,023, filed on Nov. 25, 1998, now abandoned, which is a continuation of application No. 08/727,470, filed as application No. PCT/CH94/00078 on Apr. 22, 1994, now Pat. No. 5,861,169.

(51) Int. Cl.[7] ............................................. A61K 33/42
(52) U.S. Cl. ........................ 424/601; 424/440; 426/532; 426/658; 426/660
(58) Field of Search ................................. 424/440, 601; 426/532, 658, 660

(56) References Cited

U.S. PATENT DOCUMENTS

| | | | | |
|---|---|---|---|---|
| 4,397,837 A | * | 8/1983 | Raaf et al. ..................... | 424/51 |
| 5,833,954 A | * | 11/1998 | Chow et al. ................... | 424/49 |
| 5,861,169 A | * | 1/1999 | Kaufmann ................... | 424/440 |

FOREIGN PATENT DOCUMENTS

| | | | |
|---|---|---|---|
| HU | 188643 | * | 5/1986 |
| WO | 91/07100 | * | 5/1991 |
| WO | 95/28910 | * | 11/1995 |

* cited by examiner

*Primary Examiner*—Jean C. Witz
(74) *Attorney, Agent, or Firm*—Haverstock Garrett & Roberts; Patrick Wasley; Veo Peoples

(57) ABSTRACT

An improved composition and method for plaque inhibiting hard candies, is disclosed, having alkali metal monophosphate as the improved neutralizing active ingredient.

6 Claims, No Drawings

US 6,582,731 B1

HARD CANDY WITH PLAQUE-NEUTRALIZING EFFECT COMPRISING ALKALI METAL MONOPHOSPHATE

This application is a continuation-in-part of U.S. patent application Ser. No. 09/200,023 filed Nov. 25, 1998, which is a continuation of Ser. No. 08/727,470 filed Dec. 20, 1996, now U.S. Pat. No. 5,861,169, which was the National Stage of International Application No. PCT/CH95/00078, filed Apr. 22, 1994.

BACKGROUND OF THE INVENTION

1. Field of the Invention

The invention relates to a hard candy with tooth plaque-neutralizing effect, the use of a hard candy to clean the teeth, and a process and device for manufacturing a hard candy. The term hard candy is generally understood to mean oval compressed lozenges, chewable candies, pastilles capsules, tablets, and similar presentations.

2. Background of the Prior Art

After the consumption of food and stimulants, tooth plaque is a particular risk, due to the resulting acids. In particular, sugars cause and promote dental caries, and it is currently considered to be scientifically proven that carious lesions are the result of a process that affects the surface of teeth. The fermentation of orally administered carbohydrates into organic acids, in bacterial tooth plaque, and the related drop in the pH of that plaque are of primary importance for the formation of caries.

To neutralize tooth plaque acids, alkaline compounds, such as sodium carbonate, bicarbonate, and ammonium phosphate, as well as ureas, have been recommended to counter the organic acids that are formed by the fermentation of carbohydrates. However, the salts and sometimes bitter taste of those buffers has made it difficult to use them. For example, EP-525 388 describes the manufacture and composition of a tablet having the aim of producing a slight foaming action to improve the taste of tablets containing active pharmaceutical ingredients, particularly calcium and magnesium. U.S. Pat. No. 4,409,202 describes a tablet or candy whose aim is to cover or neutralize mouth odor. The main active ingredient is a vegetable oil. U.S. Pat. No. 5,250,569 proposes the use of amino acids, including in connection with toothpastes, to avoid the unpleasant taste of orally-administered aluminum compounds. It would then be possible to produce special rhinitis medications containing aluminum. Another aim of that US patent is to produce a slow-release effect for aluminum. Finally, JP-A-69 13281 suggests the manufacture of tablets to clean the mouth and deodorize the breath.

The most effective mechanical method of inhibiting caries is to clean the teeth with toothpaste and a toothbrush after every occasion on which stimulants or food are consumed. However, it is not always possible to clean the teeth with toothpaste and a brush after every meal or every time food is consumed. That is particularly the case when away from home, traveling, at work, and the like.

Against that background, so-called plaque-neutralizing chewing gums have been offered as an alternative for some time. They are intended both to stimulate the flow of saliva, as a result of chewing movements, and to contain the aforementioned active ingredients, which cause a buffer action in the saliva, or result in neutralization of the acids produced during the fermentation of carbohydrates. Those chewing gums have the advantage that they can be used immediately after eating and, to a great extent, can neutralize the acids that damage the teeth. That may be done, by stimulating the flow of saliva, whereby an increased buffer capacity is produced; by promoting the neutralization of plaque acids; by increasing the distribution of saliva in difficult to reach interdental spaces; by improved removal of food particles from the oral cavity; by creating a pH value that promotes remineralization of the tooth enamel; or finally, by promoting remineralization via stimulating the flow of saliva with an increased mineral content.

Such chewing gums are also useful, for example, for patients with temporary or chronically limited mobility, which generally leads to poorer oral hygiene. In addition, when taking medications that inhibit the flow of saliva, the aforementioned chewing gum can be a useful tool for improving oral hygiene.

However, the problem with such plaque-neutralizing chewing gums is that gum chewing is socially unacceptable to many people, or is rejected for other reasons, for example in the presence of dental prostheses, synthetic teeth, and the like. Therefore, one aim of the present invention is to create an alternative to chewing gum that increases neutralization of acid plaque, thereby preventing or at least inhibiting formation of caries in the presence of plaque.

Hard candy with plaque-neutralizing effect that contain at least one active ingredient that neutralizes acid to a great extent, have been considered in the past for a number of reasons. A principle desired advantage of the hard candy is that the problems described in connection with chewing gums are eliminated. For example, it is known that when chewing gum, the active ingredients are released by strong chewing during the first 1.9 minutes, but very few of the effective neutralizing substances are released by the chewing gum after 2.0 minutes, which retards the neutralizing effect. In contrast, a hard candy that would better distribute the dose of neutralizing active ingredient, could last up to 5–6 minutes. Moreover, the stimulation of saliva flow should be nearly identical to that when chewing gum is used. Also, JP-A-60237947 discloses a special encapsulated air bubble appearance for candy in order to promote a refreshing perceived effect.

The prior art active ingredients for hard candies have been alkaline metal salts, and alkaline earth metal salts, in particular polyphosphates, carbonates, hydrocarbonates, and hydrogen phosphates. However these prior art candy formulations have several drawbacks in so far as their use of phosphate is concerned.

In the past Mr. Austin Wagenknicht disclosed the use of a restricted class of phosphates, in U.S. Pat. No. 4,170,632, for plaque inhibiting hard candies. However, the types of phosphates used were the same as those formulated for chewing gums, i.e., polyphosphates including pyrophosphates, orthophosphates, tripolyphosplates and hexametaphosphates in amounts of at least 1% by weight, and preferably 2% to about 20%. In addition, it was disclosed that dental abrasives, which may be dicalcium diphosphate dihydrate, or sodium metaphosphate, or tricalcuim phospate might also be included in amounts of 1% to 30% preferably 1.5% to about 20%. In practice, the threshold amount of acid-neutralizing material was at least, that amount needed to neutralize and establish a pH of between about 5.5 to about 10 in the oral cavity, preferably pH about 6 to 9.

A plaque inhibiting active ingredients formulation, effective in hard candies, at lesser amounts than the prior art would be a welcomed but surprising advancement over chewing gum type formulations.

SUMMARY OF THE INVENTION

It is therefore a principle object of the present invention to provide improved plaque inhibiting neutralizing ingredients.

This principle object and other objects will become apparent from the following detailed description, examples and claims which are fulfilled by utilizing alkali metal monophosphates, as the active ingredient in plaque inhibiting hard candies. We have discovered that these materials, surprisingly, can be effective and at lower concentrations than the prior art polyphosphates.

DETAILED DESCRIPTION AND PREFERRED EMBODIMENTS

In accordance with the improved composition of the present invention alkali metal monophosphates employed as the active neutralizing ingredient in plaque inhibiting hard candies. The alkali metal monophosphates are effective in amounts as low as 0.1% to less than about 1% by weight. The monophophates can be used in higher amounts also of up to 15%. Amounts of monophosphates of 1% to 2.0% by weight are more effective than similar amounts of polyphosphates. However, unlike polyphosphates which were required to be use at 1.0% or higher, the monophosphates are effective at a lower threshold amount. The alkali metal monophosphates which are particularly preferred are disodium hydrogen phosphate (sodium phosphate dibasic), potassium dihydrogen phosphate (potassium phosphate monobasic).

The active ingredients of the present invention are effective alone, or if desired can be used in combination with each other or with other plaque inhibiting neutralizing agents such as carbonates, bicarbonates (hydrocarbonates).

To cover the occasionally salty, soapy, or bitter taste of those acid-neutralizing active ingredients, sugar substitutes or sugar replacements and sweeteners are preferably added to the hard candy in accordance with the invention. In that regard, examples include isomalt, sorbitol, acesulfam, lycasine, sweeteners containing cyclamate, aspartame, etc.

Moreover, it has proven beneficial to add xylitol as an addition to the acid-neutralizing active ingredient, because xylitol also has a certain inhibiting effect on plaque formation, particularly in conjunction with the aforementioned active ingredient.

In addition to the aforementioned substances or active ingredients, the hard candies in accordance with the invention contain at least one carrier, as well as one or more taste-imparting flavoring agents, such as peppermint flavor, orange flavor, and the like.

To manufacture a hard candy in accordance with the invention, it is suggested to use a fundamentally known process for manufacturing candy, although it is suggested to select a temperature that does not exceed 135° C., preferably 80° C., during the metered addition of the acid-neutralizing active ingredients to the candy manufacturing mass. It has been shown in practice that in general the active substances that are essential to the invention at least partially decompose or are broken down at temperatures higher than the specified level of 135° C.

For that reason, in accordance with the invention a device or equipment for manufacturing a hard candy is suggested that is fundamentally based on a device or equipment usually used for manufacturing hard candies. It is essential to the invention that subsequent to the cooking vessel, such as for example as cooking coil, where the various basic materials, such a as carriers, water, sugar substitutes, and the like are cooked and mixed at approximately 160° C. and over, the mass is cooled by an additional cooler to a temperature from approximately 130–135° C. The proposed additional cooler is generally not included in such equipment. The metered addition of the acid-neutralizing active ingredients occurs after said additional cooling, as suggested above.

The invention will now be explained in greater detail below using experiments in which the neutralizing candy, mode in accordance with the invention, was given to a series of test subjects at the Dental Institute of the University of Zurich and confirmed the neutralizing effect of the candy. The results obtained by the Dental Institute of the University of Zurich are explained in greater detail in the Examples.

EXAMPLES

The applicant for the present invention retained the Division of Preventive Dentistry, Periodontology and Caries of the Dental Institute of the University of Zurich to perform various tests on a sample of the described neutralizing candy in accordance with the invention to determine its tooth-protecting characteristics and its plaque-neutralizing effect.

The recipes for the neutralizing candy that were used contained the ingredients shown in the following tables 1 to 12:

TABLE 1

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 1.0043 |
| Sugar Substitutes: | | | |
| Isomalt (95% D.M.) | 1,038.1666 | 986.2583 | 97.8400 |
| Xylitol | 6.5000 | 6.5000 | 0.6448 |
| Sodium Phosphate Dibasic | 2.1500 | 2.1500 | 0.2133 |
| Peppermint Flavour | 2.0000 | 2.0000 | 0.1984 |
| Acesulfam K | 1.0000 | 1.0000 | 0.0992 |
| | 1,233.6499 | 1,008.0321 | 100.0000 |

TABLE 2

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.9917 |
| Sugar Substitutes: | | | |
| Isomalt (95% D.M.) | 1,038.1666 | 986.2583 | 96.6084 |
| Xylitol | 6.5000 | 6.5000 | 0.6367 |
| Sodium Phosphate Dibasic | 15.0000 | 15.0000 | 1.4693 |
| Peppermint Flavour | 2.0000 | 2.0000 | 0.1959 |
| Acesulfam K | 1.0000 | 1.0000 | 0.0980 |
| | 1,246.4999 | 1,020.8821 | 100.0000 |

TABLE 3

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.8573 |
| Sugar Substitutes: | | | |
| Isomalt (95% D.M.) | 1,038.1666 | 986.2583 | 83.5188 |
| Xylitol | 6.5000 | 6.5000 | 0.5504 |
| Sodium Phosphate Dibasic | 175.0000 | 175.0000 | 14.8194 |
| Peppermint Flavour | 2.0000 | 2.0000 | 0.1694 |
| Acesulfam K | 1.0000 | 1.0000 | 0.0847 |
| | 1,406.4999 | 1,180.8821 | 100.0000 |

TABLE 4

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 1.0037 |
| Sugar Substitutes: | | | |
| Isomalt (95% D.M.) | 1,038.1666 | 986.2583 | 97.7827 |
| Xylitol | 6.5000 | 6.5000 | 0.6444 |
| Sodium Phosphate Dibasic | 2.1500 | 2.1500 | 0.2132 |
| Potassium Phosphate Monobasic | 0.5900 | 0.5900 | 0.0585 |
| Peppermint Flavour | 2.0000 | 2.0000 | 0.1983 |
| Acesulfam K | 1.0000 | 1.0000 | 0.0991 |
| | 1,234.2399 | 1,008.6221 | 100.0000 |

TABLE 5

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.9949 |
| Sugar Substitutes: | | | |
| Isomalt (95% D.M.) | 1,038.1666 | 986.2583 | 0.6388 |
| Xylitol | 6.5000 | 6.5000 | 0.9002 |
| Sodium Phosphate Dibasic | 9.1600 | 9.1600 | 0.2457 |
| Potassium Phosphate Monobasic | 2.5000 | 2.5000 | 0.1966 |
| Peppermint Flavour | 2.0000 | 2.0000 | 0.1966 |
| Acesulfam K | 1.0000 | 1.0000 | 0.0983 |
| | 1,243.1599 | 1,017.5421 | 100.0000 |

TABLE 6

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.8264 |
| Sugar Substitutes: | | | |
| Isomalt (95% D.M.) | 1,038.1666 | 986.2583 | 80.5081 |
| Xylitol | 6.5000 | 6.5000 | 0.5306 |
| Sodium Phosphate Dibasic | 172.0000 | 172.0000 | 14.0403 |
| Potassium Phosphate Monobasic | 47.1600 | 47.1600 | 3.8497 |
| Peppermint Flavour | 2.0000 | 2.0000 | 0.1633 |
| Acesulfam K | 1.0000 | 1.0000 | 0.0816 |
| | 1,450.6599 | 1,225.0421 | 100.0000 |

TABLE 7

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 1.0032 |
| Sugar Substitutes: | | | |
| Isomalt (95% D.M.) | 1,038.1666 | 986.2583 | 97.7333 |
| Xylitol | 6.5000 | 6.5000 | 0.6441 |
| Sodium Phosphate Dibasic | 2.1500 | 2.1500 | 0.2131 |
| Sodium Bicarbonate | 1.1000 | 1.1000 | 0.1090 |
| Peppermint Flavour | 2.0000 | 2.0000 | 0.1982 |
| Acesulfam K | 1.0000 | 1.0000 | 0.0991 |
| | 1,234.7499 | 1,009.1321 | 100.0000 |

TABLE 8

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.9961 |
| Sugar Substitutes: | | | |
| Isomalt (95% D.M.) | 1,038.1666 | 986.2583 | 97.0362 |
| Xylitol | 6.5000 | 6.5000 | 0.6395 |
| Sodium Phosphate Dibasic | 7.0000 | 7.0000 | 0.6887 |
| Sodium Bicarbonate | 3.5000 | 3.50000 | 0.3444 |
| Peppermint Flavour | 2.0000 | 2.0000 | 0.1968 |
| Acesulfam K | 1.0000 | 1.0000 | 0.0984 |
| | 1,241.9999 | 1,016.3821 | 100.0000 |

TABLE 9

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.8537 |
| Sugar Substitutes: | | | |
| Isomalt (95% D.M.) | 1,038.1666 | 986.2583 | 83.16666 |
| Xylitol | 6.5000 | 6.5000 | 0.5481 |
| Sodium Carbonate | 100.0000 | 100.0000 | 8.4325 |
| Sodium Bicarbonate | 80.0000 | 80.0000 | 6.74360 |
| Peppermint Flavour | 2.0000 | 2.0000 | 0.1687 |
| Acesulfam K | 1.0000 | 1.0000 | 0.0843 |
| | 1,411.4999 | 1,185.8821 | 100.0000 |

TABLE 10

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 1.0040 |
| Sugar Substitutes: | | | |
| Isomalt (95% D.M.) | 1,038.1666 | 986.2583 | 97.8109 |
| Xylitol | 6.5000 | 6.5000 | 0.6446 |
| Sodium Carbonate | 1.4000 | 1.4000 | 0.1388 |
| Sodium Bicarbonate | 1.0500 | 1.0500 | 0.1041 |
| Peppermint Flavour | 2.0000 | 2.0000 | 0.1983 |
| Acesulfam K | 1.0000 | 1.0000 | 0.0992 |
| | 1,233.9499 | 1,008.3321 | 100.0000 |

TABLE 11

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.9924 |
| Sugar Substitutes: | | | |
| Isomalt (95% D.M.) | 1,038.1666 | 986.2583 | 96.6747 |
| Xylitol | 6.5000 | 6.5000 | 0.6371 |
| Sodium Carbonate | 8.0000 | 2.1500 | 0.7842 |
| Sodium Bicarbonate | 6.3000 | 2.0000 | 0.6175 |
| Peppermint Flavour | 2.0000 | 2.0000 | 0.1960 |
| Acesulfam K | 1.0000 | 1.0000 | 0.0980 |
| | 1,245.7999 | 1,020.1821 | 100.0000 |

TABLE 12

RECIPE NEUTRALIZATION CANDY

| Raw Material | Weighted in Quantity in kg | Weighted in Quantity in Final Product With appr. 99% Dry Matter | Weighted in Quantity in 100 g/% Candy Candy Weight 1.8 g |
|---|---|---|---|
| Water Potable | 183.8333 | 10.1238 | 0.8759 |
| Sugar Substitutes: | | | |
| Isomalt (95% D.M.) | 1,038.1666 | 986.2583 | 85.3252 |
| Xylitol | 6.5000 | 6.5000 | 0.5623 |
| Sodium Carbonate | 100.0000 | 100.0000 | 8.6514 |
| Sodium Bicarbonate | 50.0000 | 50.0000 | 4.3257 |
| Peppermint Flavour | 2.0000 | 2.0000 | 0.1730 |
| Acesulfam K | 1.0000 | 1.0000 | 0.0865 |
| | 1,381.4999 | 1,155.8821 | 100.0000 |

The tests for each recipe were done on eight test subjects in excellent health. They had already participated in previous tests, and the physiological conditions in their oral cavities were known in detail to the researchers.

The test prostheses were cleaned and inserted and the test subjects were instructed to continue with their normal eating habits during the test but to refrain from any oral hygiene on the lower jaw. They were allowed to rinse with water to remove food particles and to use a toothbrush without toothpaste on the upper jaw. Not removing the prostheses allowed undisrupted growth of plaque on the membrane surfaces of the interdentally installed electrodes.

The test results showed that the buffering food additives added to the candy in accordance with the invention are capable of quickly neutralizing acidified plaque caused by carbohydrate fermentation subsequent to a sucrose rinse, thereby limiting the harmful effect of the sucrose. The test results showed that monophosphates are effective at lower amounts than 1% by weight, although they can be effective at higher amounts as well, and in higher amounts are more effective than would be predicted from polyphosphates.

Of course, the recipes set forth above for manufacturing a hard candy or neutralizing candy in accordance with the invention are for the purpose of providing a more detailed explanation of the invention. Obviously the formulations can be changed, varied, or added to in accordance with the measures set forth in the Claims.

It is fundamentally surprising that a hard candy that has a monophosphate neutralizing or cleansing effect can be used to improve the result obtained using the polyphosphate from chewing gum formulations.

What is claimed is:

1. A method for neutralizing plaque, said method comprising sucking on hard candy, which candy comprises a single phase preparation of up to about 15% by weight alkali metal monophosphates formed by the steps of:

(a) mixing together carriers, water, and sugar substitutes;

(b) heating the mixture of the carriers, water, and sugar substitutes to 80° C.;

(c) cooking the mixture of the carriers, water, and sugar substitutes at a temperature over 160° C.;

(d) cooling the cooked mixture by transferring the mixture to an additionally provided cooler and cooling the mixture to a temperature lower than 135° C.

(e) adding at least 0.1% by weight alkali metal monophosphate acid neutralizing active ingredient and an effective amount of xylitol to the mixture cooled below 135° C.; and, (f) shaping the cooled mass containing the acid neutralizing active ingredient into said hard candy.

2. The method of claim 1, wherein said acid neutralizing active ingredient is in an amount of from about 0.1% by weight of said candy composition to less than 1.0%.

3. The method of claim 1, wherein said active ingredient is in an amount of from about 1% to about 2.5% by weight.

4. The method of claim 1, wherein the mixture is heated to about 80° C. before heating to over 160° C.

5. The method of claim 1 or claim 2, wherein the monophosphate is sodium phosphate dibasic or potassium phosphate monobasic.

6. The method of claim 3 or 1, wherein the monophosphate is sodium phosphate dibasic or potassium phosphate monobasic.

* * * * *